(12) United States Patent
Yamashita et al.

(10) Patent No.: US 7,381,979 B2
(45) Date of Patent: Jun. 3, 2008

(54) ROTATING IRRADIATION APPARATUS

(75) Inventors: Tsutomu Yamashita, Hitachi (JP); Shigeji Kaneko, Hitachi (JP); Hiroshi Saga, Takahagi (JP); Norio Takeda, Kashiwa (JP)

(73) Assignee: Hitachi, Ltd., Tokyo (JP)

( * ) Notice: Subject to any disclaimer, the term of this patent is extended or adjusted under 35 U.S.C. 154(b) by 169 days.

(21) Appl. No.: 11/472,387

(22) Filed: Jun. 22, 2006

(65) Prior Publication Data
US 2007/0023699 A1 Feb. 1, 2007

(30) Foreign Application Priority Data
Jun. 30, 2005 (JP) .............................. 2005-190880

(51) Int. Cl.
*A61N 5/00* (2006.01)
*A61N 5/01* (2006.01)
(52) U.S. Cl. .................... 250/505.1; 250/492.3; 250/492.23; 378/65
(58) Field of Classification Search ............... None
See application file for complete search history.

(56) References Cited

U.S. PATENT DOCUMENTS 7,193,227 B2 * 3/2007 Hiramoto et al. ........ 250/492.3

2006/0192072 A1 * 8/2006 Yamashita et al. .......... 248/664
2007/0215819 A1 * 9/2007 Hiramoto et al. ........ 250/492.3

FOREIGN PATENT DOCUMENTS

| JP | 11-047287 | 2/1999 |
|----|-----------|--------|
| JP | 2000-140134 | 5/2000 |
| JP | 3599995 | 9/2004 |

* cited by examiner

*Primary Examiner*—Nikita Wells
(74) *Attorney, Agent, or Firm*—Mattingly, Stanger, Malur & Brundidge, PC (57) ABSTRACT

A rotating irradiation apparatus includes a rotating gantry 3 including a front ring 19 and a rear ring 20 and is provided with a beam delivery device 11 and an irradiation device 4. The beam delivery device 11 delivers an ion beam used for particle radiotherapy. Radial support devices 61A and 61B support the front ring 19 and radial support devices 61A and 61B support the rear ring 20. Each radial support device includes a linear guide 41, an upper support structure disposed above the linear guide 41, and a lower support structure disposed below the linear guide 41. The upper support structure is movably mounted on the lower support structure and is movable in the direction of the rotational axis of the rotating gantry 3.

36 Claims, 8 Drawing Sheets

ROTATING IRRADIATION APPARATUS

BACKGROUND OF THE INVENTION

The present invention relates to a rotating irradiation apparatus, and more particularly to a rotating irradiation apparatus suitable for irradiating an affected area with an ion beam.

An ion beam irradiation system is a particle radiotherapy system used to irradiate an affected area with a proton beam or an ion beam of carbon ions, etc. to treat cancer. The ion beam irradiation system includes a rotating gantry, which is a rotating irradiation device. For example, the rotating gantry includes a front ring, a rear ring, and a gantry body connected between the front and rear rings, as indicated in Japanese Patent Laid-open No. 11-47287. The gantry body is provided with an irradiation device (or irradiation nozzle) and a beam delivery device (or beam path) for guiding an ion beam. The front and rear rings are supported by their respective radial support devices each including a plurality of rotatable rollers. More specifically, each roller provided in each radial support device supports the front or rear ring. Some of the rollers supporting the rear ring are rotated by a motor to rotate the rotating gantry. This rotation of the rotating gantry contributes to directing the irradiation device in an ion beam irradiation direction to irradiate an affected area with an ion beam.

Japanese Patent Laid-open No. 2000-140134 discloses a rotating gantry for a particle radiotherapy system, in which the rear ring is supported by a support device including rollers, and the front ring is supported through a rotating ring by the front support frame mounted on the base portion. The rotating ring allows the front ring to be rotatably mounted on the front support frame. The front support frame, in turn, is mounted on a leg portion rotatably connected to the base portion by pins. These pins enable the leg portion to be tilted in the direction of the rotational axis of the rotating gantry. Therefore, the rear ring also can be tilted in the direction of the rotational axis of the rotating gantry. A bed is mounted on the front support frame. This arrangement can prevent misalignment between the bed and the rotating gantry.

Japanese Patent No. 3599995 also describes a rotating gantry for a particle radiotherapy system. This rotating gantry includes two rotating rings each supported by rollers. Further, in order to maintain the rotational center position of this rotating gantry within a predetermined tolerance over an extended period of time, at least one of these rotating rings is rotated by a pair of drive rollers that sandwich the rotating ring and that are in contact with respective sides of the rotating ring.

The particle radiotherapy system is designed to irradiate a target position on an affected area with an ion beam for treatment. To increase the accuracy of treatment, it is desirable that the irradiation position does not change as the rotating gantry rotates. In reality, however, as the rotating gantry rotates, the ion beam irradiation position moves three-dimensionally in a whirl due to the distortion of the rotating gantry caused by the weight of the deflection electromagnet, etc. provided on the rotating gantry. The center of this three-dimensional whirl of the irradiation position is referred to as the "isocenter" or "irradiation target center". One of the fundamental performance requirements for the particle radiotherapy system is that the ion beam irradiation position only moves, or whirls, within a sphere with a diameter of a few millimeters centered at the isocenter as the rotating gantry rotates.

One method for maintaining the ion beam irradiation position close to the isocenter to thereby satisfy the above requirement is to reduce the distortion of the gantry body connected between the front and rear rings by constructing it such that it has a highly rigid structure. This greatly reduces the three-dimensional whirling of the ion beam irradiation position.

Figure 1A:
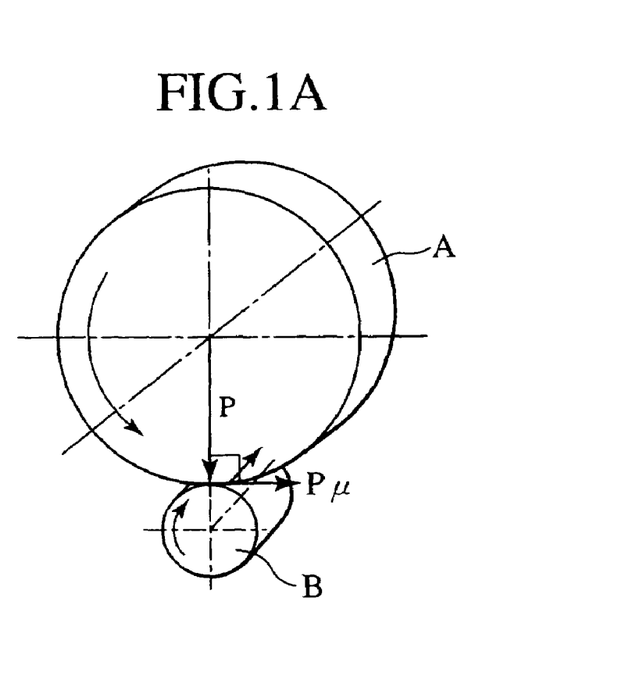
FIG. 1A is a diagram showing a roller A and a roller B that are rotating in contact with each other.
Figure 1B:
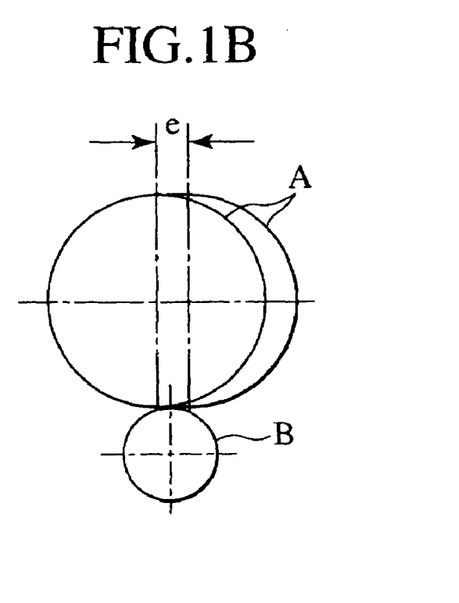
FIG. 1B is a diagram showing displacement of the rotational axis of the roller A.
Figure 1C:
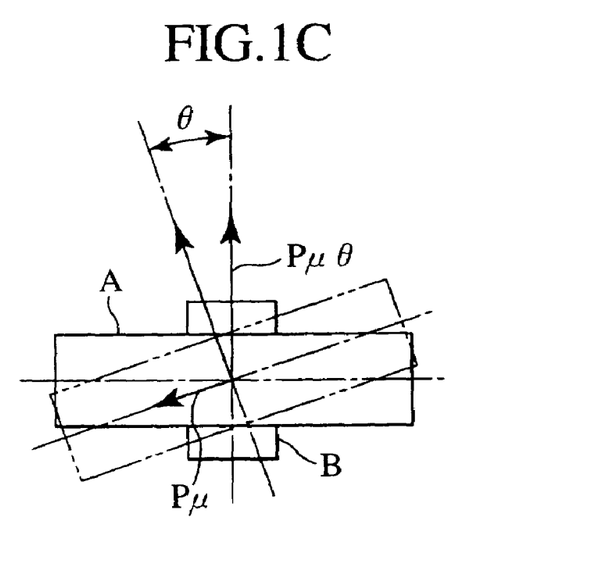
FIG. 1C is a top view of the roller A showing the axial component of force produced due to the displacement of the rotational axis of the roller A.

There is another factor in causing an error in the irradiation position. This factor cannot be removed by increasing the rigidity of the rotating gantry body. For example, if the rotational axes of the rotatable rollers of the radial support devices are fully parallel to those of the front and rear rings, the rotating gantry does not move in the axial direction on its own when it rotates. In reality, however, the rotational axes of the rollers of the radial support devices are not fully parallel to those of the front and rear rings due to the following factors: (a) errors in the machining and assembly of components of the rotating gantry; (b) adjustment errors during installation of the rotating gantry; (c) deterioration of the building with age; and (d) small variations in height, etc. due to wear of the rings and rollers. Thus, there is a certain degree of misalignment between the rotational axes of the rollers and the rings. As a result, the gantry tries to move in the axial direction due to the axial component of the rotational force applied to the engagement surfaces of the rollers, as shown in FIGS. 1A to 1C. (This movement is referred to as a "skewing movement".) Assume that a roller A (corresponding to a rear ring 20 described later) is rotating in contact with a roller B (corresponding to a roller 22 described later) having a smaller diameter than the roller A, as shown in FIG. 1A. In this case, if P denotes the weight of the roller A and $\mu$ denotes the friction coefficient between the rollers A and B, then the roller rotational force produced in the direction as indicated in FIG. 1A is $P*\mu$. If the rotational axis of the roller A is displaced by an amount e as shown in FIG. 1B due to the reasons stated above, then the axial component of the roller rotational force $P*\mu$ is $P*\mu*\theta$, as shown in FIG. 1C (where $\theta$ denotes the angle at which the rotational axis of the roller A is displaced from that of the roller B). This axial component force $P*\mu*\theta$ causes the roller A to move in the axial direction.

The radial support devices described in Japanese Patent Laid-open No. 11-47287 are fixed to the mounting base portion, which prevents them from moving in the axial direction of the rotating gantry. As a result, the rotating gantry itself moves in the axial direction or a horizontal direction as it rotates, resulting in increased three-dimensional whirling of the irradiation position.

In one method for reducing the movement of the rotating gantry in the axial direction, the rotating gantry is mounted between two thrust support devices. These thrust support devices press the outer sides of the front and rear rings against the rotating gantry in the opposite axial directions to restrain the movement of the rotating gantry in the axial direction. With this method, however, the thrust support devices receive large reactive force, making it necessary to considerably increase their rigidity. Furthermore, the larger the axial thrust force applied by the thrust support devices, the larger the friction between the rings of the rotating gantry and the thrust rollers of the thrust support devices and hence the larger the required rotational driving force. Further, an increase in the axial thrust force results in an increase in the wear of the thrust rollers of the radial support devices and the front and rear rings, promoting the movement of the rotating gantry in the axial direction.

In another method for reducing the movement of the rotating gantry in the axial direction, the rollers of the radial support devices do not have the ability to rotate the rotating gantry. Instead, the apparatus is provided with a mechanism for performing both a rotational driving function and a braking function, as indicated in Japanese Patent No.3599995. Thus, to reduce the "skewing movement" of the rotating gantry, the radial support devices are dedicated to supporting the weight of the rotating gantry, while the drive mechanism rotates the gantry. However, this method still cannot prevent occurrence of skewing due to the factors (a) to (d) above.

For example, in the case of the structure shown in FIG. 4 of Japanese Patent No. 3599995, gear teeth are formed on the peripheral portion of a rotating ring and engaged with the pinion coupled to the motor to rotate the rotating gantry. In this structure, however, there is a backlash in the mesh between the gear teeth and the pinion even right after they are installed, and furthermore this backlash increases with time due to their wear. As a result, it is difficult to maintain sufficient rotation angle accuracy of the rotating gantry (for example, a stopping accuracy of ±0.25 degree or better). Further, there is an increasing need for an inching function to adjust the rotational position of the rotating gantry by rotating the gantry by a small angle based on positional information obtained from an image of the affected area portion after positioning of the rotating gantry at a predetermined angle. However, due to the above backlash, the rotation angle of the rotating gantry needs to be adjusted each time the rotational direction of the gantry is reversed, making it difficult both to achieve a rotation angle accuracy of ±0.25 degree or better without spending time and to achieve the inching function.

Skewing occurs due to the factors (a) to (d) above even with the gantry structure shown in Japanese Patent Laid-open No. 2000-140134, as well as with the structure shown in FIG. 1 of Japanese Patent No. 3599995 in which drive rollers are brought into contact with the sides of the rotating rings to rotate the rotating gantry.

In order to increase the irradiation beam positioning accuracy of the rotating gantry (that is, to maintain the irradiation position close to the isocenter), and maintain the increased accuracy, it is important to provide the rotating gantry with capabilities to remove the factors (a) to (d) above.

Specifically, the capability to accommodate dimensional errors due to the factors (a) and (b) as much as possible allows accurate alignment to be easily achieved. Further, the ability to quickly detect and easily correct misalignment between the rotational axes due to the factors (c) and (d) (or changes that may slowly occur over a long period of time) allows reducing the installation adjustment and maintenance time of the rotating gantry. Therefore, a rotating irradiation apparatus employing a rotating gantry with these capabilities can achieve high throughput.

SUMMARY OF THE INVENTION

An object of the present invention is to provide a rotating irradiation apparatus capable of treating an increased number of patients per year.

To accomplish the above object, the present invention provides a rotating irradiation apparatus comprising: a rotatable body provided with an irradiation device; a plurality of thrust support devices for limiting movement of the rotatable body in the direction of the rotational axis of the rotatable body; a first rotating body support device including a plurality of rotatable rollers for supporting one end portion of the rotatable body, the rotatable rollers being in contact with the rotatable body; and a second rotating body support device including a plurality of rotatable rollers for supporting the other end portion of the rotatable body, the rotatable rollers being in contact with the rotatable body; wherein the first rotating body support device or both the first and second rotating body support devices are movable in the direction of the rotational axis.

Thus, the above rotating irradiation apparatus of the present invention is configured such that: the plurality of thrust support devices restrain the movement of the rotating body (or rotatable body) in the direction of its rotational axis; and the first rotating body support device or both the first and second rotating body support devices are movable in the direction of the rotational axis. This arrangement allows the movable rotating body support device or devices to be moved to accommodate the relative axial movement between the rotating body and the rollers supporting the rotating body due to misalignment between their axes. Therefore, the movement of the rotating body itself in the direction of its rotational axis is considerably reduced, resulting in a great reduction in the three-dimensional whirling of the irradiation position. This considerably increases the positioning accuracy of the ion beam emitted from the irradiation device, enabling the ion beam to be accurately directed to the area to be treated. Furthermore, it is possible to focus the ion beam onto the area to be treated, resulting in a reduction in the treatment time and hence an increase in the number of patients that can be treated a year. That is, a particle radiotherapy system employing the rotating irradiation apparatus of the present invention can achieve high throughput.

The present invention allows a particle radiotherapy system to treat an increased number of patients per year.

BRIEF DESCRIPTION OF THE DRAWINGS

Other objects and advantages of the invention will become apparent from the following description of embodiments with reference to the accompanying drawings in which:

FIGS. 1A, 1B and 1C are diagrams illustrating how skewing occurs in a rotating irradiation apparatus according to the present invention, wherein.

FIGS. 5A, 5B and 5C are diagrams showing the configuration of a linear guide in detail, wherein.

FIGS. 6A and 6B are diagrams showing the arrangement of guide rollers shown in FIG. 2, wherein

DETAILED DESCRIPTION OF THE PREFERRED EMBODIMENT

Rotating irradiation apparatuses according to preferred embodiments of the present invention will now be described with reference to the accompanying drawings.

First Embodiment

A rotating irradiation apparatus according to a first embodiment of the present invention will be described with reference to FIGS. 2 to 6A and 6B. The rotating irradiation apparatus of the first embodiment is a structure included in a particle radiotherapy system (or ion beam irradiation system). The rotating irradiation apparatus includes a rotating gantry 3, rotating body support devices 2A and 2B, an irradiation device 4, a beam delivery device 11, a motor (a rotational drive device) 30, a front thrust support device 46, and a rear thrust support device 47. The rotating gantry 3 includes a cylindrical gantry body 18, a front ring (a first annular member) 19 provided on the front end portion of the gantry body 18, and a rear ring (a second annular member) 20 provided on the rear end portion of the gantry body 18. Thus, the front ring 19 is disposed on the side from which a treatment table 13 is inserted into the treatment chamber (not shown) formed within the gantry body 18. The beam delivery device 11 is disposed on the gantry body 18. The gantry body 18 includes the irradiation device 4 for irradiating the patient with the ion beam delivered through the beam delivery device 11. A balancing weight 21 is provided on the gantry body 18 such that it is located 180 degrees opposite to the beam delivery device 11 and the irradiation device 4 in order to maintain the rotational balance of the rotating gantry 3.

The rotating gantry 3 is supported by the rotating body support devices 2A and 2B. Specifically, the rotating gantry 3 is supported by pluralities of rotatable rollers 22 in the rotating body support devices 2A and 2B. The rotatable rollers 22 of the rotating body support device 2A are in contact with the front ring 19, while those of the rotating body support device 2B are in contact with the rear ring 20. The structure of the rotating body support device 2A will now be described since the rotating body support device 2B has substantially the same structure as the rotating body support device 2A.

Figure 4:
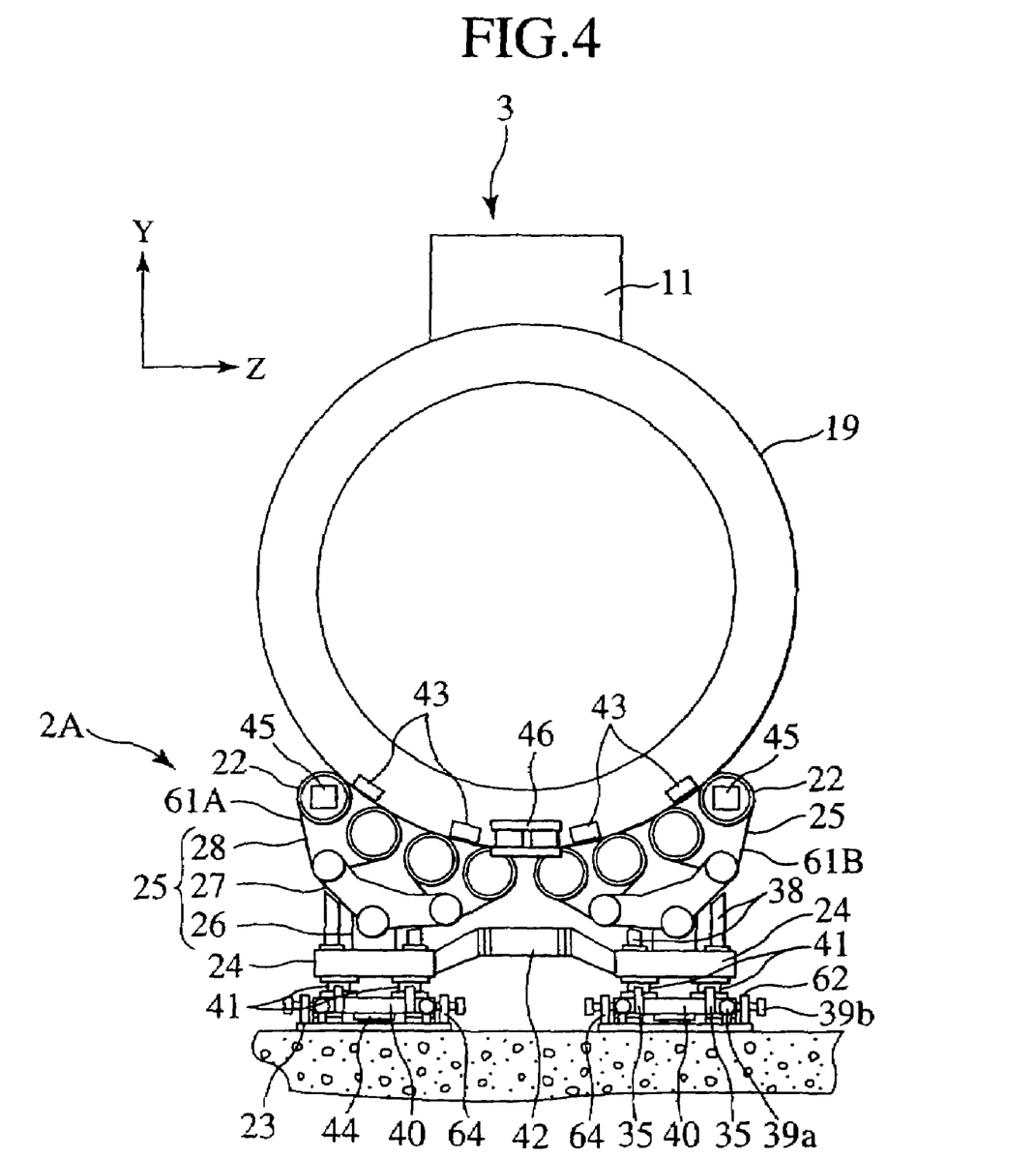
FIG. 4 is another side view showing the front side of the rotating irradiation apparatus shown in FIG. 2.

The rotating body support device 2A includes radial support devices 61A and 61B that are symmetrical to each other about a vertical line passing through the rotational axis of the rotating gantry 3, as shown in FIG. 4.

Figure 2:
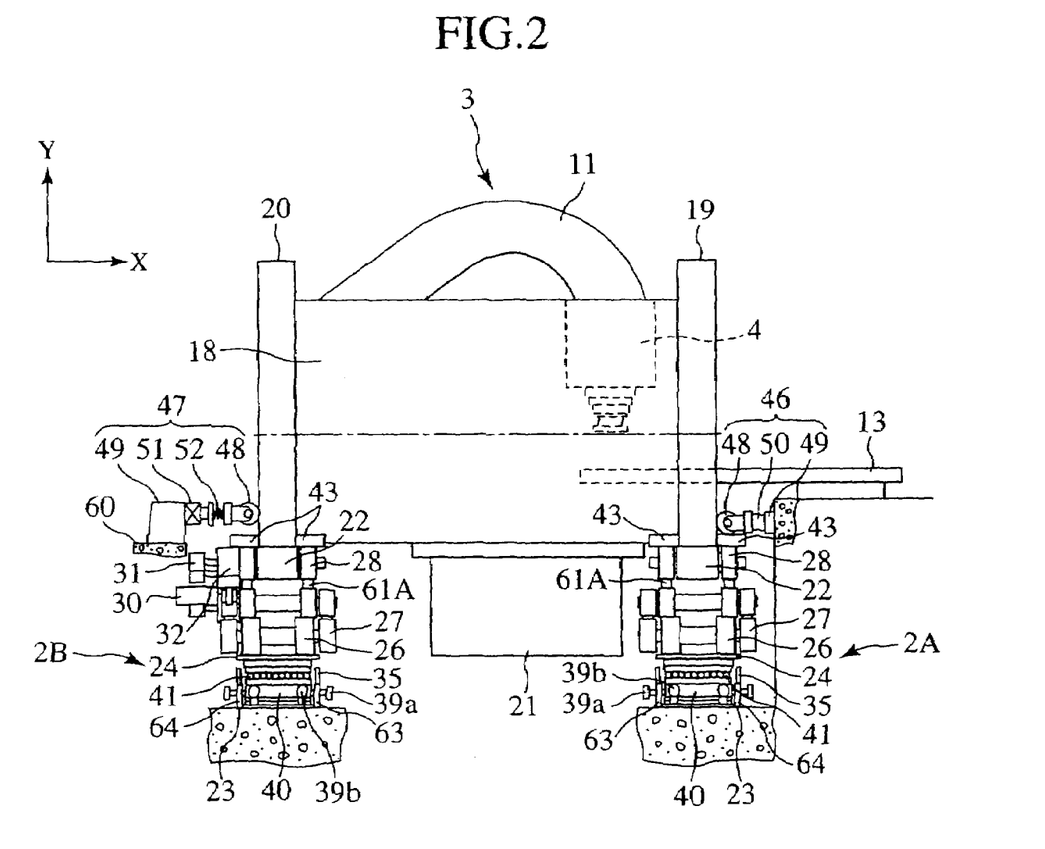
FIG. 2 is a diagram showing the configuration of a rotating irradiation apparatus according to a first embodiment of the present invention.

The radial support device 61A includes a foundation base 23, an intermediate base 40, linear guides 41, a pedestal 24, a link frame 25, and a plurality of rollers 22, as shown in FIGS. 2 and 4. The foundation base 23 is set on the floor of the building in which the particle radiotherapy system is installed. The intermediate base 40 is supported by a jack 44 mounted on the foundation base 23. The jack 44 is used to adjust the height position of the rotational axis of the rotating gantry 3. The pair of linear guides 41 are mounted on the intermediate base 40 to support the pedestal 24. The link frame 25 to which the plurality of rollers 22 are fixed is mounted on the pedestal 24. If the change in the ground level and in the building foundation level with age is expected to be a few millimeters or less, a taper liner may be used, instead of the jack 44, to adjust the height position of the axis of the rotating gantry 3. Although the taper liner allows the height position to be adjusted by only a small amount as compared to the jack, such a configuration is relatively low in cost.

The link frame 25 includes: a bracket 26 mounted on the pedestal 24; a first link member 27 rotatably attached to the bracket 26; and a pair of second link members 28 rotatably attached to the first link member 27. A plurality of rollers 22 (e.g., two rollers 22) are rotatably attached to each second link member 28. The rollers 22 attached to the pair of second link members 28 are disposed along the outer circumferential surface of the front ring 19 and support the front ring 19. In order to prevent abnormal movement of the rotating gantry 3 in directions perpendicular to its rotational axis due to an earthquake, etc., a pair of stoppers (or inclination limiting devices) 38 are provided on the pedestal 24 to restrain the first link member 27 from rotating more than a predetermined angle.

The intermediate base 40 can be moved in the direction of the rotational axis of the rotating gantry 3 and in a direction perpendicular to it. A position adjusting device 64 for the intermediate base 40 is mounted on the foundation base 23. The position adjusting device 64 includes: a first position adjusting device for adjusting the position of the intermediate base 40 in the direction of the rotational axis of the rotating gantry 3; and a second position adjusting device for adjusting the position of the intermediate base 40 in a direction perpendicular to the rotational axis. That is, the first position adjusting device is used to adjust the position of the isocenter in the axial direction, while the second position adjusting device is used to adjust the position of the rotational axis of the rotating gantry 3 in the above perpendicular direction. The first position adjusting device includes adjusting bolt support members 63 and position adjusting bolts 39a, as shown in FIG. 2. These adjusting bolt support members 63 are mounted on the foundation base 23 and arranged along the direction of the rotational axis so as to face each other across the intermediate base 40. The position adjusting bolts 39a engage with the threaded holes in the adjusting bolt support members 63.

The tip of each position adjusting bolt 39a faces one side of the intermediate base 40.

On the other hand, the second position adjusting device includes (two) adjusting bolt support members 62 and (two) position adjusting bolts 39b, as shown in FIG. 4. These adjusting bolt support members 62 are mounted on the foundation base 23 and arranged in the above perpendicular direction so as to face each other across the intermediate base 40. The position adjusting bolts 39b engage with threaded holes in the adjusting bolt support members 62. The tip of each position adjusting bolt 39b faces the opposing side of the intermediate base 40.

Figure 5A:
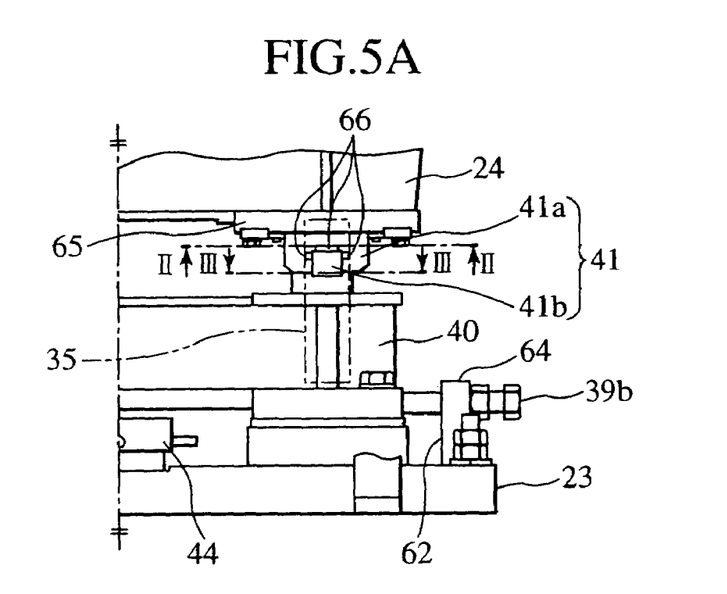
FIG. 5A is an enlarged view of a linear guide portion shown in FIGS. 3 and 4.
Figure 5B:
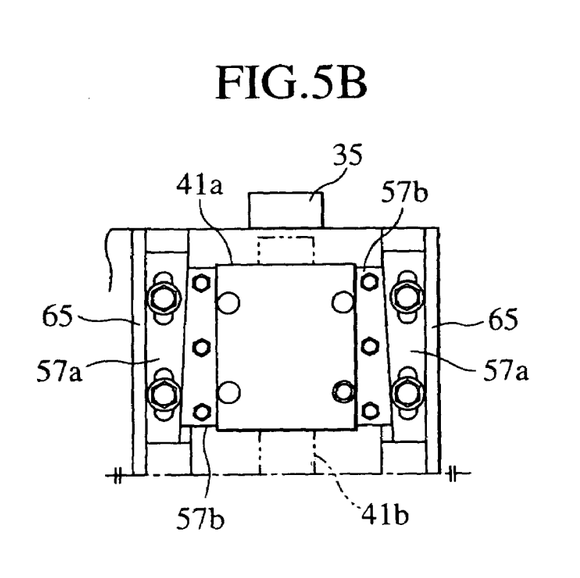
FIG. 5B is a cross-sectional view taken along line II-II of FIG. 5A.
Figure 5C:
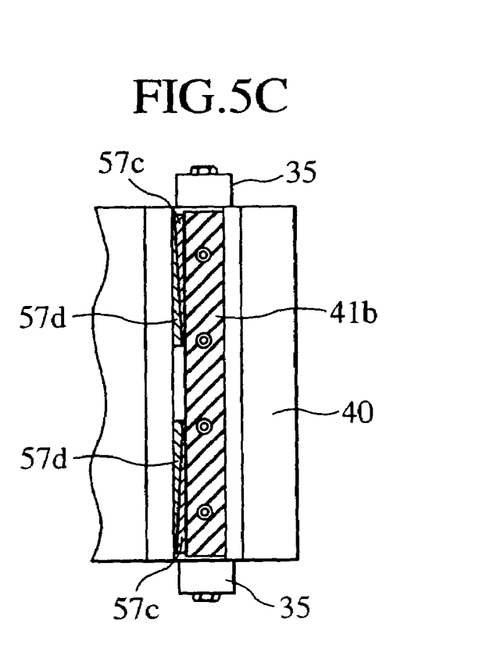
FIG. 5C is a cross-section view taken along line III-III of FIG. 5A.

The configuration of the linear guides 41 will now be described in detail. With the linear guides 41, the upper support structure of the radial support device 61A located above the linear guides 41 can be moved relative to the lower support structure of the radial support device 61A located below the linear guides 41 in the direction of the rotational axis of the rotating gantry 3. That is, the rotating gantry 3 can be freely moved in its axial direction. According to the present embodiment, the upper support structure includes the pedestal 24, the link frame 25, and the rollers 22. The lower support structure, on the other hand, includes the foundation base 23 and the intermediate base 40. More specifically, the linear guides 41 forming a pair are provided between the intermediate base 40 and the pedestal 24. Each linear guide 41 includes a guide block 41a and a linear rail 41b, as shown in FIG. 5A. The guide block 41a is mounted on the pedestal 24, while the linear rail 41b is mounted on the intermediate base 40. The linear rail 41b is disposed within a concave portion formed in the intermediate base 40 such that its length direction coincides with the direction of the rotational axis of the rotating gantry 3. The linear rail 41b is pressed against a side of the concave portion in the intermediate base 40 by use of wedges 57c and 57d. Wedges 57a and 57b forming a pair, on the other hand, are disposed between the guide block 41a and a protrusion portion 65 provided on the pedestal 24 such that sides of the wedges 57a and 57b face each other. The wedges 57a and 57b are slid in opposite directions to move the guide block 41a in the horizontal direction perpendicular to the direction of the rotational axis of the rotating gantry 3 in order to position it at a predetermined location. The linear guide 41 includes a plurality of rollers 66 between the guide block 41a and the linear rail 41b. These rollers 66 are disposed along the direction of the rotational axis of the rotating gantry 3 (i.e., the length direction of the linear rail 41b) and between sides of the linear rail 41b and the sides of the above concave portion formed in the guide block 41a and between the top of the linear rail 41b and the bottom surface of the concave portion (see FIG. 2). Thus, the guide block 41a is spaced from the linear rail 41b by the rollers 66. The rollers 66 disposed on the top of the linear rail 41b support the guide block 41a and hence the pedestal 24. To limit the distance the linear guide 41 moves in the direction of the rotational axial, a pair of stoppers (or stopper members) 35 are mounted on the intermediate base 40 such that the guide block 41a is sandwiched between these stoppers 35 on the axial end sides.

The linear guide 41 including a plurality of rollers is adapted to exhibit a friction coefficient smaller than that between the front ring 19 and the rollers 22. Further, the linear guide 41 is also adapted to be movable only in the direction of the rotational axis of the rotating gantry 3 and have a high torsional rigidity in directions perpendicular to the rotational axis. Still further, since the linear guide 41 includes rollers, it can support the heavy, high-rigidity rotating gantry 3 for an extended period of time and provide a friction equivalent to that of a conventional common linear guide in which the guide block is spaced from the rail by balls. The hertzian stress between the rollers and the guide block 41a and the linear rail 41b is smaller than that between the balls and these components. Therefore, the linear guide 41 allows the rotating gantry 3 to be smoothly moved in the direction of its rotational axis for an extended period of time. Thus, the linear guide 41 is a moving member movable in the direction of the rotational axis.

The radial support device 61B has the same structure as the radial support device 61A described above. The pedestal 24 of the radial support device 61A is coupled to that of the radial support device 61B by a distance piece 42. If these radial support devices 61A and 61B are not coupled to each other by the distance piece 42, the linear guides 41 may wear more rapidly due to the components of the force caused by the weight of the rotating gantry 3 in the horizontal direction perpendicular to the rotational axis of the rotating gantry 3. According to the present embodiment, the radial support devices 61A and 61B are coupled to each other by the distance piece 42 to allow these components of force perpendicular (horizontal) to the axial direction to cancel each other, thereby preventing the wear of the linear guides 41. Furthermore, this cancellation enables one to freely move the radial support devices 61A and 61B in the direction of the rotational axis concurrently. One roller 22 in each of the radial support devices 61A and 61B is provided with a rotation detector 45.

There will now be described the rotating body support device 2B for supporting the rear ring 20 with reference to FIGS. 2 and 3. The rotating body support device 2B also includes radial support devices 61A and 61B. The pedestal 24 of the radial support device 61A is coupled to that of the radial support device 61B by a distance piece (or coupling member) 42. In the case of the rotating body support device 2B, the radial support devices 61A and 61B each include a motor 30 attached to a roller 22 to apply a rotational force to the roller 22 through a reduction gear (not shown). The rotating gantry 3 rotates when the rotational force of these motors 30 is transmitted to it due to the friction between the rear ring 20 and the rollers 22. In the rotating body support device 61B, the other three rollers 22 in each radial support device 61A, 61B are provided with a braking device 32. When the rotating gantry 3 is rotated, air is supplied to the braking devices 32 so that the braking devices 23 do not apply braking force to the rollers 22. When the rotation of the rotating gantry 3 needs to be stopped in an emergency, on the other hand, the air is discharged from the braking devices 32 so that the braking devices apply braking force to the rollers 22. This braking force is transmitted to the rear ring 20 due to the friction between the rear ring 20 and the rollers 22, thereby stopping the rotation of the rotating gantry 3. A solenoid valve 31 is used to supply air to or discharge air from the braking devices 32. When the solenoid valve 31 is closed, the air supplied to the braking devices 32 is confined within the braking devices 32. When the solenoid valve 31 is opened, on the other hand, the air is discharged from the braking devices 32.

Figure 3:
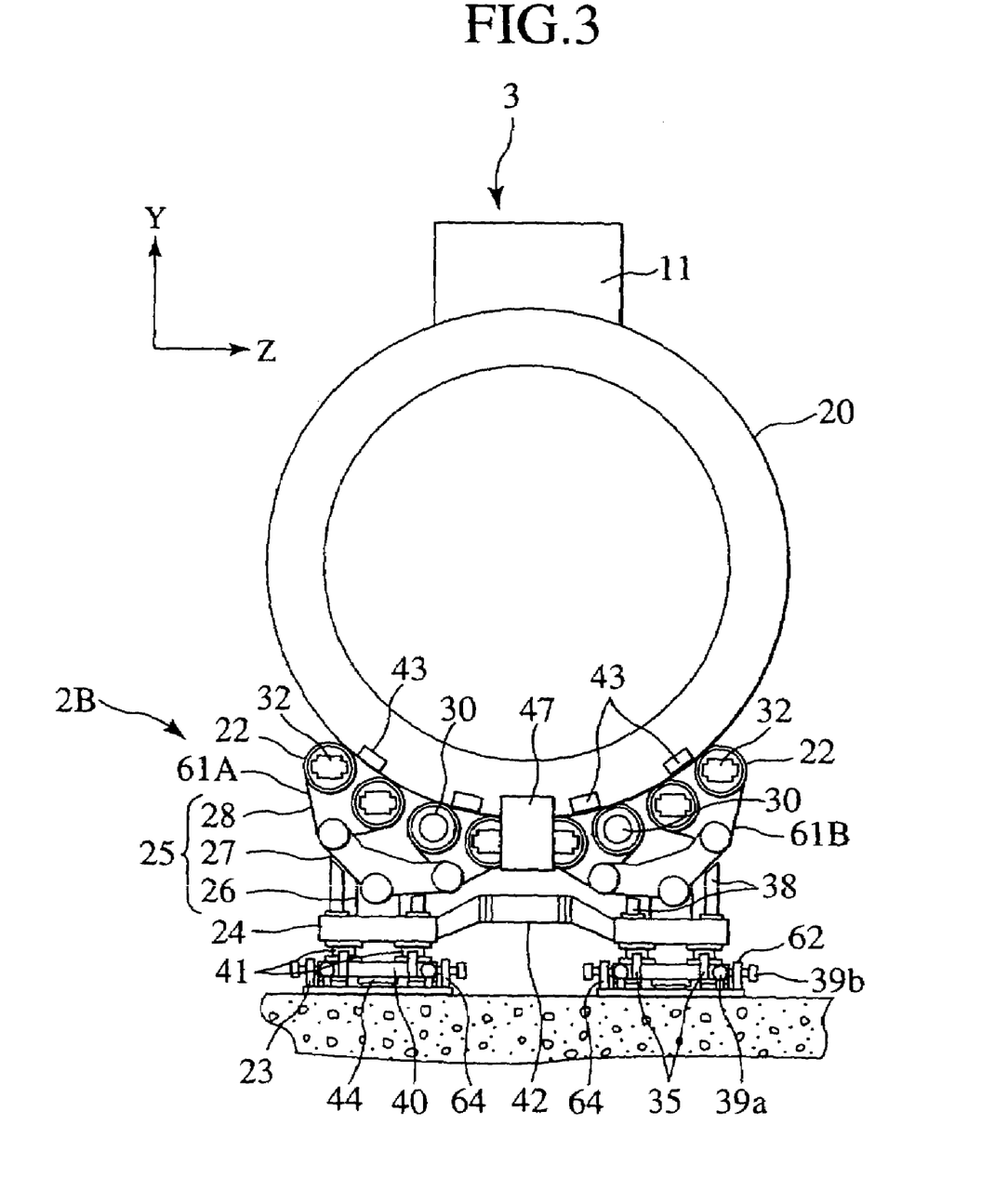
FIG. 3 is a side view showing the rear side of the rotating irradiation apparatus shown in FIG. 2.

In the rotating body support device 2B, the two rollers 22 coupled to their respective motors 30 and the six rollers 22 coupled to their respective braking devices 32 are symmetrically arranged about a vertical line passing through the rotational axis of the rotating gantry 3, as shown in FIG. 3. With this arrangement, the rotational drive force applied by the motors 30 and the braking force applied by the braking devices 32 are transmitted to the rotational gantry 3 in a balanced manner. Further, since the motors 30, the braking devices 32, and the solenoid valve 31 are disposed on the rear side of the rotating gantry 3, their maintenance is facilitated.

According to the present embodiment, the rotating body support devices 2A and 2B each include two radial support devices, and each radial support device includes two linear guides 41. However, if the rotating gantry 3, the beam delivery device 11, the irradiation device 4, etc. are relatively heavy and hence the total weight applied to each linear guide 41 exceeds its maximum allowable weight, then each radial support device may include three or more linear guides 41. Further, each linear guide 41 may include balls between the guide block 41a and the linear rail 41b, instead of rollers, allowing the radial support device to be freely moved in the axial direction.

According to the present embodiment, each of the rotating body support devices 2A and 2B includes two pedestals 24 each having a link frame 25 mounted thereon. That is, the rotating body support devices 2A supports the front ring 19 using 8 rollers 22 that are in contact with the outer peripheral surface of the front ring 19 at different locations. Likewise, the rotating body support device 2B supports the rear ring 20 using 8 rollers 22 that are in contact with the outer peripheral surface of the rear ring 20 at different locations. This arrangement in which the front ring 19 and the rear ring 20 are each supported by 8 rollers 22 reduces the movement of the rotating gantry 3 in the horizontal direction perpendicular to the rotational axis of the rotating gantry 3.

In order to reduce the movement of the rotating gantry 3 in the horizontal direction perpendicular to the rotational axis of the rotating gantry 3, the present embodiment further includes the following two features. One is that, in addition to increasing the rigidity of the link frames 25 and the pedestals 24 supporting these link frames 25, a pair of stoppers 38 are provided on each pedestal 25 in order to reduce abnormal movement of the rotating gantry 3 in directions perpendicular to the rotational axis due to an earthquake, etc. Another feature is that the linear guides 41 are configured such that the centers of the guide block 41a and the linear rail 41bcan be aligned with respect to each other using the wedges 57a to 57d. The wedges 57a and 57b are movement restraining devices used to restrain the movement of the rotating gantry 3 in directions perpendicular to its rotational axis. Further, the wedges 57c and 57d are also movement restraining devices.

When the three-dimensional whirling of the irradiation position is increased due to misalignment during installation of the rotating gantry 3 or due to the change in the building foundation level and in the ground level, etc. with age, the above devices (or structures) for reducing the movement of the rotating gantry 3 in directions perpendicular to the rotational axis of the rotating gantry 3 allow one to quickly adjust alignment to eliminate the displacement in the axial direction and thereby reduce the three-dimensional whirling.

Figures 6A, 6B, 7:
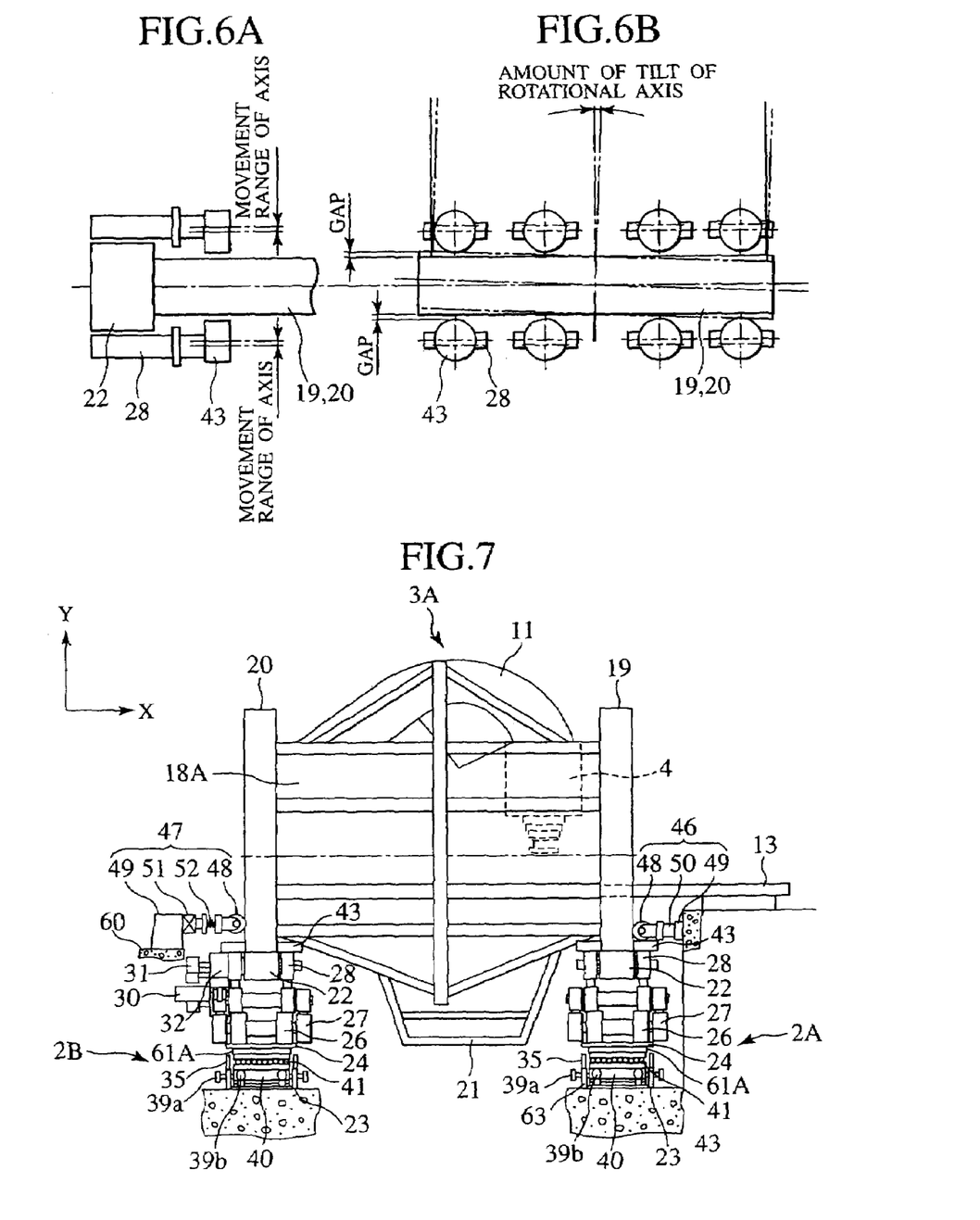
FIG. 6A is a structural diagram showing how guide rollers are mounted on a second link member.
FIG. 6B is a plan view of the guide rollers.
FIG. 7 is a diagram showing the configuration of a rotating irradiation apparatus according to a second embodiment of the present invention.

In the rotating body support devices 2A and 2B, each second link member 28 is provided with two guide rollers 43. These two guide rollers 43 are disposed so as to sandwich the front ring 19 or rear ring 20 (see FIG. 2). There is a gap between each guide roller 43 and the front ring 19 or rear ring 20 (see FIGS. 6A and 6B). This gap is essential to preventing situations where variations in the width of the front ring 19 and the rear ring 20 due to errors in the machining of these rings are constantly transmitted to the radial support devices through the guide rollers 43. However, the size of this gap must be varied depending on the errors in the machining and assembly of the components constituting the guide rollers 43, as well as on the errors in the machining of the rings. Therefore, according to the present embodiment, each guide roller 43 is mounted on the second link member 28 so as to be able to adjust the distance between the shaft supporting the guide roller 43 and the front ring 19 (or rear ring 20), as shown in FIGS. 6A and 6B. That is, the guide roller 43 is mounted on the second link member 28 such that the axis of the guide roller 43 can be moved within the axis movement range shown in FIG. 6A in the direction perpendicular to the sides of the front ring 19, or rear ring 20 (that is, the direction of the rotational axis of the rotating gantry 3). This arrangement allows the gap between the guide rollers 43 and the front ring 19 or rear ring 20 to be easily adjusted.

Since in the rotating body support device 2A each second link member 28 is provided with two guide rollers 43, the amount of tilt of the axis of the front ring 19 (or rear ring 20) can be adjusted by the 4 guide rollers 43 that are disposed at different locations along the circumference of the ring. This arrangement in which several guide rollers 43 are disposed at different locations along the circumference of the ring to align the axis of the ring allows one to finely adjust the amount of tilt of the rotating gantry 3 in the horizontal direction perpendicular to its rotational axis. The gap between each guide roller 43 and each ring must be smaller than that for the stoppers 35 for limiting the distance the radial support devices 2A and 2B can move in the direction of the rotational axis. If there is no need to finely adjust the amount of tilt of the rotational axis of the rotating gantry 3 in horizontal directions, it is not necessary to provide all second link members 28 with a guide roller 43. For example, referring to FIG. 6B, only the guide rollers 43 at the horizontal ends may be provided.

The front thrust support device 46 and the rear thrust support device 47 are disposed so as to sandwich the rotating gantry 3 in order to reduce the movement of the rotating gantry 3 in its axial direction (see FIG. 2). The front thrust support device 46 includes a roller 48, a thrust frame 49, and a buckling tube 50. The thrust frame 49 is installed on the foundation of the building. The roller 48 is rotatably attached to the buckling tube 50 such that the roller 48 is in contact with the side of the front ring 19 facing the foundation of the building. The buckling tube 50 is mounted on the thrust frame 49. The buckling tube 50 has a function to prevent damage to the roller 48 and the thrust frame 49 when abnormal thrust force is applied to the rotating gantry 3 due to an earthquake, etc. The rear thrust support device 47 includes a roller 48, a thrust frame 49, a spring 52, and a load cell (or thrust load detector) 51. This thrust frame 49 is installed on the foundation 60 of the building. The roller 48 is rotatably attached to a holding member. The spring 52 attached to the load cell 51 mounted on the thrust frame 49 is also attached to this holding member. In the rear thrust support device 47, the roller 48 is in contact with the side of the rear ring 20 facing the foundation 60. Since the spring 52 is attached in a compressed state in the direction of the rotational axis of the rotating gantry 3, the roller 48 is pressed against the rear ring 20 due to the reactive force, significantly reducing the movement of the rotating gantry 3 in the axial direction. Thus, the front thrust support device 46 and the rear thrust support device 47 are thrust movement restraining devices for restraining the movement of the rotating gantry 3 in the direction of its rotational axis.

The load cell 51 monitors the thrust force (or thrust weight) from the rotating gantry 3. This monitoring allows one to determine and adjust the mounting accuracy of the rotating gantry 3. That is, after installation of the rotating gantry 3 and the rotating body support devices 2A and 2B, the position of the rotational axis of the rotating gantry 3 is adjusted. Specifically, the height position of the rotational axis is adjusted using the jacks 44 provided in the rotating body support devices 2A and 2B. The position of the rotational axis of the rotating gantry 3 in the horizontal direction perpendicular to the rotational axis and the position of the rotating gantry 3 in the direction of the rotational axis are adjusted using the position adjusting bolts 39a of the second position adjusting devices and the position adjusting bolts 39b of the first position adjusting devices provided in the radial support devices 61A and 61B in the rotating body support devices 2A and 2B. The above positional adjustment of the rotational axis of the rotating gantry 3 is performed based on the thrust force values measured by the load cell 51. If the rotational axis of the rotating gantry 3 installed is misaligned, the thrust force values measured by the load cell 51 while rotating the rotating gantry 360 degrees considerably vary from one another. In such a case, the position of the rotational axis is adjusted by use of the position adjusting bolts 39a and 39b until the measured thrust force values become substantially equal to one another. Thus, the displacement of the rotational axis of the rotating gantry 3 can be minimized by use of the load cell 51 and the position adjusting bolts 39b and 39a. The monitoring of the thrust force by the load cell 51 is useful in monitoring occurrence of misalignment of the rotating gantry 3 due to change in the building foundation level or deterioration of the building. The monitoring of the thrust force by the load cell 51 is useful in monitoring a movement of the rotating gantry 3 in the direction of its rotational axis causing an error in the irradiation position.

The thrust weight data obtained by the load cell 51 is input to a controller (not shown). This controller stops the rotation of the motor 30 and thereby stops the rotation of the rotating gantry 3 when the detected thrust weight exceeds a predetermined value.

According to the present embodiment, the buckling tube 50 is disposed in the front thrust support device 46, and the spring 51 and the load cell 52 are disposed in the rear thrust support device 47. However, if this arrangement is difficult to achieve due to the arrangement of other components, etc., then the spring 51 and the load cell 52 may be disposed in the front thrust support device 46 and the buckling tube 50 may be disposed in the rear thrust support device 47.

There will now be briefly described how a particle radiotherapy system to which the rotating irradiation apparatus of the present embodiment is applied is used to treat cancer in a patient. This exemplary particle radiotherapy system includes a synchrotron (or cyclotron) as its accelerator. First, the rotating gantry 3 is rotated so as to align the beam path in the irradiation device 4 with the direction in which to irradiate an affected area of the patient with an ion beam. Then, the treatment table 13 on which the patient lies is moved such that the affected area is aligned with the beam path. Then, the accelerator is caused to emit an ion beam after accelerating the beam. The emitted ion beam is delivered into the beam delivery device 11 provided on the rotating gantry 3 through another beam delivery device (not shown). The ion beam then passes through the irradiation device 4 to reach the affected area of the patient on the treatment table 13.

The rotating irradiation apparatus of the present embodiment described above has the following major effects.

(1) Since the rotating irradiation apparatus of the present embodiment includes the front thrust support device 46 and the rear thrust support device 47, the movement of the rotating gantry 3 in its axial direction is limited. Further, in the rotating body support devices 2A and 2B, the radial support devices 61A and 61B each include linear guides 41. Therefore, the radial support devices 61A and 61B can be moved in the direction of the rotational axis of the rotating gantry 3. Thus, the rotating irradiation apparatus of the present embodiment is constructed such that: the movement of the rotating gantry 3 in the direction of its rotational axis is limited; and the radial support devices 61A and 61B can be moved in the direction of the rotational axis of the rotating gantry 3. Therefore, in the rotating irradiation apparatus of the present embodiment, the relative axial movement between the rotating gantry 3 and the rollers 22 supporting the rotating gantry 3 due to misalignment between the rotational axes of the rotating gantry 3 and the rollers 22 can be accommodated by moving the radial support devices in the axial direction. This means that the movement of the rotating gantry 3 itself in the axial direction is considerably reduced, resulting in a great reduction in the three-dimensional whirling of the irradiation position. As a result, the positioning accuracy of the ion beam emitted from the irradiation device 4 is considerably increased, allowing the ion beam to be accurately directed to the affected area of the patient on the treatment table 13. Furthermore, it is possible to focus the ion beam on the affected area, resulting in a reduction in the treatment time per patient and hence an increase in the number of patients that can be treated a year. That is, a particle radiotherapy system to which the rotating irradiation apparatus of the present embodiment is applied can achieve high throughput.

According to the present embodiment, since the rotating gantry 3 is disposed between the front thrust support device 46 and the rear thrust support device 47, the movement of the rotating gantry 3 in the direction of its rotational axis can be firmly restrained. Therefore, the movement of the rotating gantry 3 in the direction of its rotational axis can be limited to a small range. In this state, the radial support devices can be moved in the axial direction, making it possible to considerably reduce the relative axial movement between the rollers 22 and the rotating gantry 3 due to occurrence of skewing.

In each radial support device, the linear guides 41 may be disposed between the foundation base 23 and the floor of the building, instead of between the intermediate base 40 and the pedestal 24. This arrangement also allows the radial support devices to be moved in the direction of the rotational axis, thereby increasing the ion beam positioning accuracy, as compared to conventional arrangements. According to the present embodiment, the radial support devices 61A and 61B each include an upper support structure and a lower support structure, and the upper support structure can be moved in the direction of the rotational axis by use of the linear guides 41. Since the linear guides are disposed between the intermediate base 40 and the pedestal 24, the weight of the upper support structure is significantly lighter than the weight of the lower support structure including the foundation base 23. Therefore, the linear guides 41 can be of a small size, resulting in a great reduction in their friction coefficient. Accordingly, with the above configuration of the radial support devices including the upper support structure, the rollers 22 can be more readily moved to accommodate the relative axial movement between the rollers 22 and the rotating gantry 3 due to misalignment between the rotational axes of the rollers 22 and the rotating gantry 3.

(2) Since the rotating irradiation apparatus of the present embodiment includes movement restraining devices (e.g., the combination of the wedges 57a and 57b and the combination of the wedges 57c and 57d) to restrain the movement of the rotating gantry 3 in the horizontal direction perpendicular to the rotational axis of the rotating gantry 3, the misalignment between the rotational axes of the rotating gantry 3 and the rollers 22 of the radial support devices 61A and 61B can be significantly reduced. The radial support devices, which include rollers for supporting the weight of the rotating gantry 3, try to move in a direction perpendicular to the rotational axis of the rotating gantry 3 due to the component of force produced by the weight of the rotating gantry 3 in that direction. However, the movement restraining devices of the present embodiment can restrain the movement of the rotational axis of the rotating gantry 3 in that perpendicular direction. Therefore, it is possible to increase the positioning accuracy of the irradiation ion beam on the affected area of the patient on the treatment table 13 positioned in place.

(3) In each rotating body support device of the rotating irradiation apparatus of the present embodiment, the pedestal 24 of the radial support device 61A is coupled to that of the radial support device 61B by the distance piece (or coupling member) 42. Therefore, the distance piece (or coupling member) 42 receives from the radial support devices 61A and 61B the components of force produced by the weight of the rotating gantry 3 in the horizontal direction perpendicular to the rotational axis of the rotating gantry 3. As a result, these components of force cancel each other and hence the radial support devices 61A and 61B are unlikely to move independently, as compared to when no coupling member is used. This enables the radial support devices 61A and 61B, coupled to each other by the coupling member 42, to be moved in parallel to each other in the direction of the rotational axis concurrently. Further, the radial support devices 61A and 61B are easy to move, since no components of force perpendicular to the rotational axis are applied to them.

(4) Since the radial support devices 61A and 61B include rotational drive mechanisms (or motors 30) and braking mechanisms (or braking devices 32), the components of force causing the relative axial movement between the rollers 22 and the rotating gantry 3 are increased due to machining and assembly errors and adjustment errors during installation. However, according to the present embodiment, the radial support devices 61A and 61B including the rotational drive mechanisms and the braking mechanisms may be adapted to be able to move at least in the direction of the rotational axis to achieve the effects described in (1) above.

(5) The stoppers 38 can limit rotational movement of each first link member 27 due to an earthquake, etc. to within a permissible range.

(6) Since stopper members (stoppers 35) are disposed so as to limit the movement of the rollers 22 in their rotational axis, the movement of the radial support devices 61A and 61B in the direction of the rotational axis can be limited even if the guide rollers 43 are damaged due to an earthquake, etc. Therefore, the rollers 22 can be prevented from being displaced from the outer circumferential surface of the rear ring 20 (or front ring 19) in the direction of the rotational axis, allowing the rotating gantry 3 to be constantly supported on the rollers 22. It should be noted that the distance that the stoppers 35 allow the rotating gantry 3 to move in the direction of its rotational axis must be larger than the gaps between the front ring 19 (or rear ring 20) and the guide rollers 43, which are provided to limit the amount of tilt of the rotating gantry 3 in the horizontal direction perpendicular to the rotational axis. The reason for this is that if weight is applied to a stopper or stoppers 35 due to movement of the rotating gantry 3 in the direction of its rotational axis caused by skewing movement of the rotating gantry 3, the axial movement of the radial support devices is restrained, which might distort the roller frames and hence increase the degree of skew.

(7) Since the rear thrust support device 47 includes the load cell (or thrust load detector) 51, the mounting accuracy of the rotating gantry 3 can be determined and adjusted based on the thrust load values measured by the load cell 51. Further, the measured thrust load values may be compared with the thrust load value obtained when the rotating gantry 3 was initially positioned in order to detect occurrence of misalignment of the rotating gantry 3 due to change in the building foundation level, deterioration of the building, etc.

(8) The position adjusting device 64 allows one to adjust the position of the rotational axis of the rotating gantry 3 in the horizontal direction perpendicular to the rotational axis and the position of the rotating gantry 3 in the direction of the rotational axis and thereby increase the mounting accuracy of the rotating gantry 3. The position adjusting device 64 also allows one to correct the misalignment of the rotating gantry 3 due to the change in the building foundation level, deterioration of the building, etc. with age. When the rotating gantry 3 is installed, it may be positioned based on thrust load values measured by the load cell 51, resulting in increased mounting accuracy of the rotating gantry 3.

(9) The first link members 27 and the second link members 28 in the radial support devices 61A and 6B reduce the load differences between the rollers 22 that support the weight of the rotating gantry 3, allowing the diameter of the rollers 22 to be reduced. The reduction in the diameter of the rollers 22 in turn allows the reduction ratio of the combination of the rollers 22 and the rotating gantry 3 to be increased, leading to a reduction in the capacity of the motors 30 and in the size of the braking devices 32. Further, since the rotating gantry 3 is rotated and braked using the friction between the rollers 22 and the rear ring 20 (or front ring 19) of the rotating gantry 3, smooth rotation control of the rotating gantry 3 can be achieved without any backlash, as compared to when gears are used to rotate and brake the rotating gantry 3. Further, such a drive force transmission system using friction allows the angular position of the rotating gantry 3 to be finely adjusted.

(10) Since the controller stops the rotation of the motors 30 if the thrust load value measured by the load cell 51 exceeds a predetermined value, it is possible to prevent an increase in the damage to the rotating gantry 3, etc. Further, the rotating irradiation apparatus may be adapted to give an alarm when the measured thrust load value exceeds a predetermined value.

(11) The radial support devices 61A and 61B on the side of the front ring 19 (which do not include motors 30) each include a rotation detector 45 provided on a roller 22. This arrangement allows for rotation control of the rotating gantry 3 using the motors 30 based on the outputs of two or more rotation detectors 45. This makes it possible to monitor or detect abnormal events, such as failure of one rotation detector 45 and breakage of a bearing of a radial support device, and thereby achieves secure rotation control. According to the present embodiment, the rotation detectors 45 are provided on rollers 22 in the radial support devices 61A and 61B on the side of the front ring 19, instead of on rollers 22 in the radial support devices 61A and 61B on the side of the rear ring 20, which include rotational drive mechanisms and braking mechanisms. This allows the rotation angle to be accurately detected without being affected by slippage between the rollers 22 and the rotating gantry 3.

(12) The plurality of guide rollers 43 may be arranged along the outer circumferences of the front ring 19 and the rear ring 20 such that the front and rear rings are sandwiched between the guide rollers 43 and there are appropriate gaps between the guide rollers 43 and these rings. This allows reducing the amount of tilt of the rotating gantry 3 in the horizontal direction perpendicular to its rotational axis. Furthermore, it is possible to reduce the movement of the rotating gantry 3 in the direction of the rotational axis. As a result, the three-dimensional whirling of the irradiation position can be reduced. Ideally, in each rotating body support device, the guide rollers 43 are perpendicular to the rollers 22 in the respective radial support devices. This means that no gap may be provided between the guide rollers 43 and the front ring 19 (or rear ring 20) to constantly align the rotational axis of the rotating gantry 3 in a horizontal direction.

However, since the large machined parts making up the rotating irradiation apparatus of the present embodiment are produced with some machining errors, the apparatus inevitably has some distortion. Therefore, if no gap is provided between the guide rollers 43 and the front and rear rings, the axes of the rotating gantry 3 and the rollers 22 are misaligned with respect to each other due to this distortion. Therefore, to accommodate the distortion caused by machining errors (in the width direction of the rings provided on the rotating gantry), gaps may be provided between the guide rollers 43 and the front and rear rings and finely adjusted so as to limit the amount of tilt of the rotational axis of the rotating gantry 3 in horizontal directions and thereby reduce the movement of the rotating gantry 3 in the direction of its rotational axis.

Second Embodiment

A rotating irradiation apparatus according to a second embodiment of the present invention will be described with reference to FIG. 7. The rotating irradiation apparatus of the second embodiment is a variation of the rotating irradiation apparatus of the first embodiment, in which the rotating gantry 3 is replaced by a rotating gantry 3A. All other components are similar to those described in connection with the first embodiment. The rotating gantry 3A includes a gantry body 18A and a front ring 19 and a rear ring 20 provided on respective ends of the gantry body 18A. Unlike the gantry body 18 of the first embodiment, the gantry body 18A has a truss structure. Since the gantry body 18A has a truss structure, it has lower rigidity but lighter weight than the gantry body 18. Since the gantry body 18A has lighter weight, the size of the rotating body support devices 2A and 2B can be reduced.

This embodiment also has the effects described in (1) to (12) above in connection with the first embodiment.

Third Embodiment

Figure 8:
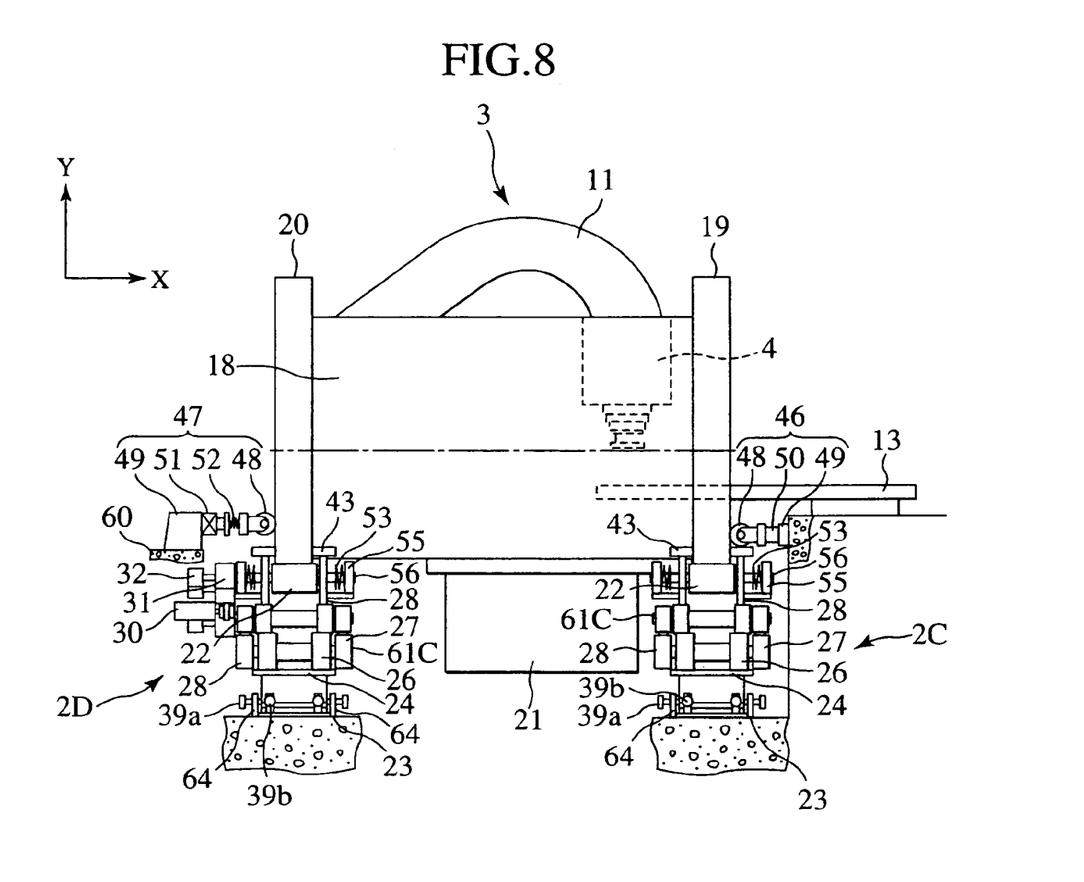
FIG. 8 is a diagram showing the configuration of a rotating irradiation apparatus according to a third embodiment of the present invention.

A rotating irradiation apparatus according to a third embodiment of the present invention will be described with reference to FIGS. 8 and 9. The rotating irradiation apparatus of the third embodiment is a variation of the rotating irradiation apparatus of the first embodiment, in which the rotating body support devices 2A and 2B are replaced by rotating body support devices 2C and 2D. All other components are similar to those described in connection with the first embodiment. The rotating body support devices 2C and 2D include a radial support device 61C shown in FIG. 8 and a radial support device 61D not shown in FIG. 8, respectively. The radial support device 61C is disposed at the same position as the radial support device 61A shown in FIGS. 3 and 4, while the radial support device 61D is disposed at the same position as the radial support device 61B shown in FIGS. 3 and 4. Unlike the radial support devices 61A and 61B, the radial support devices 61C and 61D include roller shifters, instead of linear guides 41. Each roller shifter includes a spring 53, a support member 55, and a washer member 67. Two roller shifters are provided on each roller 22. One is disposed on one end portion of the rotational axis 56 of the roller 22, while the other roller shifter is disposed on the other end portion of the rotational axis 56 of the roller 22 (see FIGS. 8 and 9). The rotational axis 56 rotatably passes through the second link members 28. The support member 55 is mounted on the second link member 28. One end of the rotational axis 56 is supported by the bearing 54 provided in the support member 55 of one roller shifter 68A, while the other end is supported by the bearing 54 provided in the support member 55 of the other roller shifter 68B. The washer member 67 is disposed on the rotational axis 56 between the second link member 28 and the bearing 54. The spring 53 is disposed between the washer member 67 and the bearing 54 and encircles the rotational axis 56. Although, unlike the first embodiment, the present embodiment does not employ stoppers 35, the second link members 28 function as the stoppers 35, instead.

The radial support devices 61C and 61D each include a foundation base 23, a pedestal 24, a link frame 25, and a plurality of rollers 22 in addition to roller shifters 68A and 68B. The pedestal 24 is mounted on the foundation base 23 set on the floor of the building, and the link frame 25 is mounted on the pedestal 24. Each link frame 25 includes a bracket 26, a first link member 27, and second link members 28, as in the first embodiment. The rollers 22 are attached to the second link members 28 through the support members 55. The radial support devices 61C and 61D also include stoppers 38 provided on the pedestals 24.

The roller shifters 68A and 68B are provided for each roller 22 in the rotating body support devices 2C and 2D. They allow the rollers 22 to be moved with respect to support structures in the radial support devices 61C and 61D in the direction of the rotational axis of the rotating gantry 3. These support structures each include the foundation base 23, the pedestal 24, and the link frame 25. Since, unlike the radial support devices 61A and 61B, the radial support devices 61C and 61D do not require intermediate bases 40 and hence are made up of fewer parts, the time required to mount them can be reduced.

The springs 53 allow the rollers 22 to freely move in the direction of the rotational axis such that they do not leave the outer circumferential surface of the front ring 19 (or the rear ring 20). However, the spring constant of the springs 53 must be set such that the rollers 22 can be moved in the axial direction by a force smaller than the force required to cause slippage between the contact surfaces of the rollers 22 and the rings in the axial direction. The roller shifters 68A and 68B may be provided for only the rollers 22 in the radial support devices 61C and 61D of the rotating body support device 2C, since these radial support devices include a rotational drive mechanism and a braking mechanism, which tend to cause a skewing movement.

Since the present embodiment employs the roller shifters 68A and 68B, the rollers 22 can move freely in the direction of the rotational axis. Therefore, if skewing occurs due to misalignment between the rotational axes of the rotating gantry 3 and the roller 22, the roller 22 can move in the direction of the rotational axis to accommodate the movement of the rotating gantry 3 in the direction of the rotational axis. As a result, in the rotating irradiation apparatus of the present embodiment, the three-dimensional whirling of the irradiation position due to skewing of the rotating gantry can be reduced, as in the first embodiment.

Figure 10:
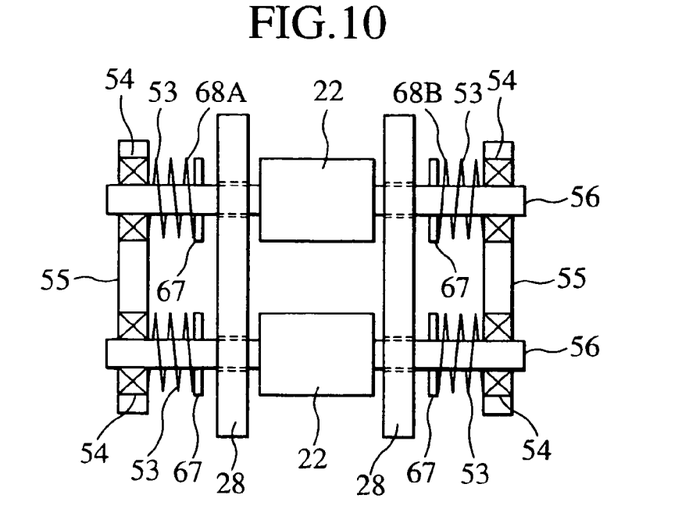
FIG. 10 is a diagram showing the configuration of another roller support structure.

Another example of a roller shifter will be described with reference to FIG. 10. In this example, the same support member 55 is used for each two adjacent rollers 22 disposed along the circumference of the rear ring 19 or the front ring 20. This arrangement allows the total number of support members 55 to be reduced, resulting in a reduction in the time required to mount all support members 55 on the second link members 28.

This embodiment also has the effects described in (1) to (12) above in connection with the first embodiment.

Fourth Embodiment

Figure 9:
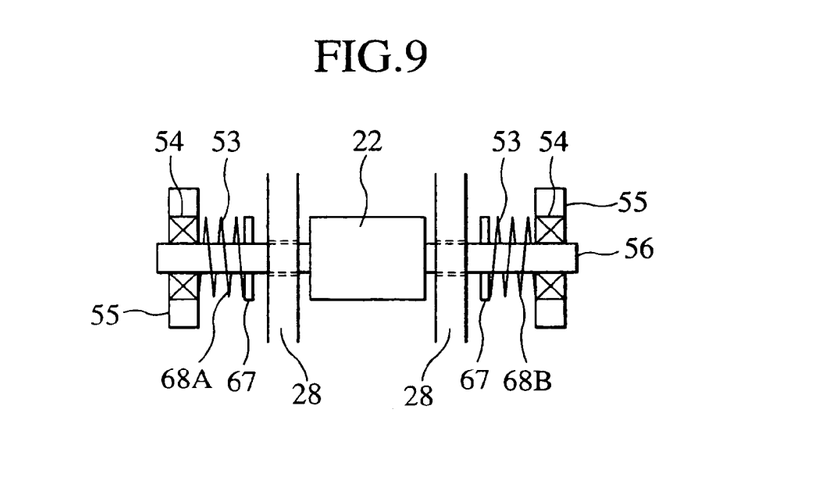
FIG. 9 is an enlarged view of a roller and components adjacent thereto in a radial support device shown in FIG. 8.
Figure 11:
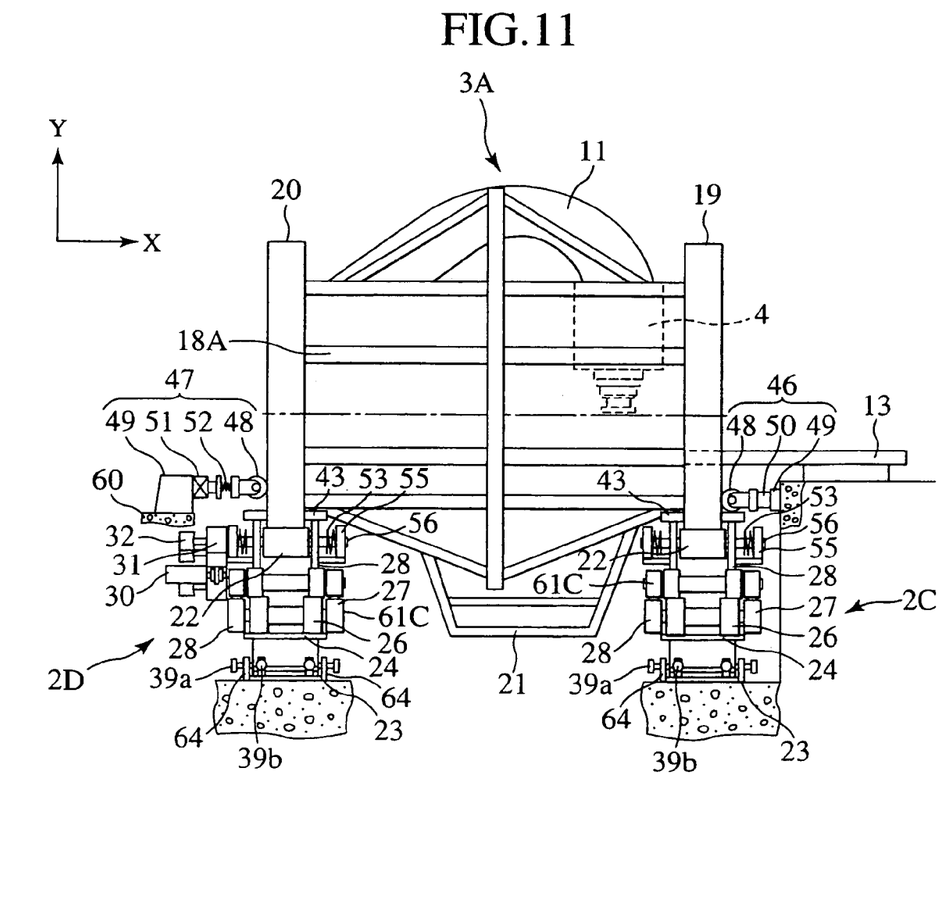
FIG. 11 is a diagram showing the configuration of a rotating irradiation apparatus according to a fourth embodiment of the present invention.

With reference to FIG. 11, there will now be described another exemplary rotating irradiation apparatus to which the roller shifters 68A and 68B shown in FIG. 9 are applied. The rotating irradiation apparatus according to a fourth embodiment of the present invention is a variation of the rotating irradiation apparatus of the third embodiment, in which the rotating gantry 3 is replaced by the rotating gantry 3A (shown in FIG. 7) described in connection with the second embodiment. All other components are similar to those described in connection with the third embodiment.

This embodiment also has the effects described in (1) to (12) above in connection with the first embodiment.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:

1. A rotating irradiation apparatus comprising:
a rotatable body provided with an irradiation device and a beam delivery device, said irradiation device emitting an ion beam, said beam delivery device delivering said ion beam into said irradiation device;
a first rotating body support device including a plurality of rotatable rollers for supporting one end portion of said rotatable body, said rotatable rollers being in contact with said rotatable body;
a second rotating body support device including a plurality of rotatable rollers for supporting the other end portion of said rotatable body, said rotatable rollers being in contact with said rotatable body;
a drive device for rotating one or more of said plurality of rollers in said first rotating body support device; and
a plurality of thrust support devices for limiting movement of said rotatable body in the direction of the rotational axis of said rotatable body;
wherein said first rotating body support device or both said first and second rotating body support devices are movable in said direction of said rotational axis.

2. The rotating irradiation apparatus as claimed in claim 1, wherein:
each said rotating body support device movable in said direction of said rotational axis includes an upper support structure and a lower support structure, said upper support structure including said plurality of rollers, said lower support structure supporting said upper support structure; and
said upper support structure is movably mounted on said lower support structure and is movable in said direction of said rotational axis.

3. The rotating irradiation apparatus as claimed in claim 2, wherein said upper support structure is mounted on a moving member mounted on said lower support structure, said moving member being movable in said direction of said rotational axis.

4. The rotating irradiation apparatus as claimed in claim 1, wherein:
each said rotating body support device movable in said direction of said rotational axis includes a support structure for supporting said plurality of rollers; and
said plurality of rollers are movably mounted on said support structure and are movable in said direction of said rotational axis.

5. The rotating irradiation apparatus as claimed in claim 1, wherein each said rotating body support device movable in said direction of said rotational axis includes a movement restraining device for restraining movement of said rotatable body in a direction perpendicular to said rotational axis.

6. The rotating irradiation apparatus as claimed in claim 1, wherein each said rotating body support device movable in said direction of said rotational axis includes a braking device attached to one or more of said rollers.

7. The rotating irradiation apparatus as claimed in claim 1, wherein each said rotating body support device movable in said direction of said rotational axis includes a roller support member and an inclination limiting device, said roller support member supporting said rollers, said inclination limiting device limiting inclination of said roller support member with respect to said rotational axis of said rotatable body.

8. The rotating irradiation apparatus as claimed in claim 1, wherein:
said rotatable body is provided with an annular member supported by said rollers; and
each said rotating body support device movable in said direction of said rotational axis includes a stopper member for limiting movement of said rollers in said direction of said rotational axis.

9. The rotating irradiation apparatus as claimed in claim 1, wherein said first and second rotating body support devices each include a position adjusting device for adjusting the positions of said rotatable body in said direction of said rotational axis and in a direction perpendicular to said rotational axis of said rotatable body.

10. The rotating irradiation apparatus as claimed in claim 1, wherein:
said first rotating body support device includes a first radial support device and a second radial support device, each radial support device including said plurality of rollers;
said second rotating body support device includes said first radial support device and said second radial support device;
said drive device is coupled to one or more of said rollers in said first and second radial support devices of said first rotating body support device; and
said first and second radial support devices in each said rotating body support device movable in said direction of said rotational axis are movable in said direction of said rotational axis.

11. The rotating irradiation apparatus as claimed in claim 10, wherein:
said first and second radial support devices movable in said direction of said rotational axis each include an upper support structure and a lower support structure, said upper support structure including said plurality of rollers, said lower support structure supporting said upper support structure; and
said upper support structure is movably mounted on said lower support structure and is movable in said direction of said rotational axis.

12. The rotating irradiation apparatus as claimed in claim 11, wherein said upper support structure is mounted on a moving member mounted on said lower support structure, said moving member being movable in said direction of said rotational axis.

13. The rotating irradiation apparatus as claimed in claim 11, wherein said first and second rotating body support devices each include a coupling member for coupling said upper support structure of said first radial support device and said upper support structure of said second radial support device together.

14. The rotating irradiation apparatus as claimed in claim 10, wherein said first and second radial support devices movable in said direction of said rotational axis each include a movement restraining device for restraining movement of said rotatable body in a direction perpendicular to said rotational axis.

15. The rotating irradiation apparatus as claimed in claim 10, wherein said first and second radial support devices movable in said direction of said rotational axis each include a braking device attached to one or more of said rollers.

16. The rotating irradiation apparatus as claimed in claim 10, wherein said first and second radial support devices movable in said direction of said rotational axis each include a roller support member and an inclination limiting device, said roller support member supporting said rollers, said inclination limiting device limiting inclination of said roller support member with respect to said rotational axis of said rotatable body.

17. The rotating irradiation apparatus as claimed in claim 10, wherein:
said rotatable body is provided with an annular member supported by said rollers; and
said first and second radial support devices movable in said direction of said rotational axis each include a stopper member for limiting movement of said rollers in said direction of said rotational axis.

18. The rotating irradiation apparatus as claimed in claim 10, wherein said first and second radial support devices each include a position adjusting device for adjusting the positions of said rotatable body in said direction of said rotational axis and in a direction perpendicular to said rotational axis of said rotatable body.

19. The rotating irradiation apparatus as claimed in claim 1, wherein:
said first and second radial support devices movable in said direction of said rotational axis each include a support structure for supporting said plurality of rollers; and
said plurality of rollers are movably mounted on said support structure and are movable in said direction of said rotational axis.

20. The rotating irradiation apparatus as claimed in claim 1, wherein said rotatable body is disposed between said plurality of thrust support devices.

21. The rotating irradiation apparatus as claimed in claim 20, wherein one or more of said plurality of thrust support devices include a thrust load detector.

22. The rotating irradiation apparatus as claimed in claim 21, further comprising:
a controller for stopping said drive device when a thrust load detected by said thrust load detector exceeds a preset value, said drive device rotating said rollers.

23. The rotating irradiation apparatus as claimed in claim 1, wherein:
said rotatable body includes a first annular member and a second annular member;
said first rotating body support device supports said first annular member, and said second rotating body support device supports said second annular member;
said first and second rotating body support devices each include a pair of guide rails spaced apart from each other in the axial direction of said rotatable body; and
said first annular member is disposed between said pair of guide rails in said first rotating body support device, and said second annular member is disposed between said pair of guide rails in said second rotating body support device.

24. The rotating irradiation apparatus as claimed in claim 23, wherein a plurality of said pairs of guide rollers are disposed along the circumferences of said first and second annular members.

25. A rotating irradiation apparatus comprising:
a rotatable body which has first and second annular members, the rotatable body rotates about a rotational axis;
an irradiation device provided within the rotatable body and which irradiates an ion beam;
a beam delivery device which delivers the ion beam to the irradiation device;
a first rotating body support device, including a plurality of rollers, which supports the first annular member, the rollers being in contact with the first annular member;
a second rotating body support device, including a plurality of rollers, which supports the second annular member, the rollers being in contact with the second annular member;
a drive device which rotates one or more of the plurality of rollers in the first rotating body support device; and
a plurality of thrust support devices for limiting movement of the rotatable body in only the direction of the rotational axis of the rotatable body,
wherein the first rotating body support device or both the first and second rotating body support devices are movable in only the direction of the rotational axis, and the plurality of thrust support devices are separately provided from one or more of the plurality of rollers driven by the drive device.

26. The rotation irradiation apparatus as claimed in claim 25, wherein the rotatable body is disposed between the plurality of thrust support devices.

27. The rotating irradiation apparatus as claimed in claim 25, wherein the first or second rotating body support device includes a linear guide being movable in only the direction of the rotational axis.

28. The rotating irradiation apparatus as claimed in claim 25, wherein the first or second rotating body support device includes roller shifters which support the rollers so as to be movable in only the direction of the rotational axis.

29. The rotating irradiation apparatus as claimed in claim 25, wherein:
each rotating body support device movable in the direction of the rotational axis includes a stopper for limiting movement in the direction of the rotational axis to within a predetermined range.

30. A rotating irradiation apparatus comprising:
a rotatable body which has first and second annular members, the rotatable body rotates about a rotational axis;
an irradiation device provided within the rotatable body and which irradiates an ion beam;
a beam delivery device which delivers the ion beam to the irradiation device;

a first rotating body support device, including a plurality of rollers, which supports the first annular member, the rollers being in contact with the first annular member;

a second rotating body support device, including a plurality of rollers, which supports the second annular member, the rollers being in contact with the second annular member;

a drive device which rotates one or more of the plurality of rollers in the first rotating body support device; and wherein a force of skewing resulting from misalignment of a roller with respect to the rotating body is compensated for by permitting the first or second rotating body support devices to be movable in the direction of the rotational axis.

31. The rotating irradiation apparatus as claimed in claim 30,
wherein, a plurality of thrust support devices are provided for limiting movement of the rotatable body in the direction of the rotational axis of the rotatable body.

32. The rotating irradiation apparatus as claimed in claim 30,
wherein, in order to prevent the force of skewing from causing the rotatable body to move in the direction of the rotational axis, at least one of the first rotating body support device and second rotating body support device are movable in the direction of the rotational axis.

33. The rotating irradiation apparatus as claimed in claim 30, wherein the first rotating body support device or both the first and second rotating body support devices are movable in only the direction of the rotational axis.

34. The rotating irradiation apparatus as claimed in claim 30, the first or second rotating body support device includes a linear guide being movable in only the direction of the rotational axis.

35. The rotating irradiation apparatus as claimed in claim 30, the first or second rotating body support device includes roller shifters which support the rollers to be movable in only the direction of the rotational axis.

36. The rotating irradiation apparatus as claimed in claim 30, wherein:
each rotating body support device movable in the direction of the rotational axis includes a stopper for limiting movement in the direction of the rotational axis to within a predetermined range.

* * * * *